United States Patent
Hopkins et al.

(10) Patent No.: US 10,345,571 B2
(45) Date of Patent: Jul. 9, 2019

(54) INTELLIGENT LIGHT SOURCE

(71) Applicant: Karl Storz Endovision, Inc., Charlton, MA (US)

(72) Inventors: Vernon Hopkins, Worcester, MA (US); Eric Webb, Charlton, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 1360 days.

(21) Appl. No.: 14/168,846

(22) Filed: Jan. 30, 2014

(65) Prior Publication Data
US 2015/0212312 A1    Jul. 30, 2015

(51) Int. Cl.
| | | |
|---|---|---|
| *G05F 1/00* | (2006.01) | |
| *A61B 1/06* | (2006.01) | |
| *G02B 23/24* | (2006.01) | |
| *G01J 1/42* | (2006.01) | |
| *G01J 5/60* | (2006.01) | |

(52) U.S. Cl.
CPC ........ *G02B 23/2461* (2013.01); *A61B 1/0661* (2013.01); *A61B 1/0669* (2013.01); *G02B 23/2453* (2013.01); *G01J 2001/4247* (2013.01); *G01J 2005/608* (2013.01)

(58) Field of Classification Search
CPC ... A61B 1/0638; A61B 1/0646; A61B 1/0669; G02B 23/2461; G02B 23/2453; H04N 5/2254; G01J 1/0418; G01J 1/0488; G01J 1/24
USPC ................ 600/103, 111, 160, 178, 180–181; 356/66, 225, 233
See application file for complete search history.

(56) References Cited

U.S. PATENT DOCUMENTS

| | | | | |
|---|---|---|---|---|
| 4,366,529 A | * | 12/1982 | Takahashi | G03B 15/05 348/68 |
| 4,588,927 A | | 5/1986 | Kanno et al. | |
| 4,690,565 A | * | 9/1987 | Kato | G01B 11/028 356/446 |
| 4,713,683 A | * | 12/1987 | Fujimori | A61B 1/0638 348/269 |
| 4,885,635 A | * | 12/1989 | Kimura | A61B 1/00105 348/70 |
| 5,006,965 A | * | 4/1991 | Jones | G02B 6/0006 362/277 |
| 5,123,067 A | | 6/1992 | Avelange et al. | |
| 5,220,912 A | | 6/1993 | Nakasima et al. | |
| 5,642,456 A | | 6/1997 | Baker et al. | |
| 6,254,531 B1 | * | 7/2001 | Higuchi | A61B 1/045 348/68 |
| 6,320,331 B1 | * | 11/2001 | Iida | H05B 37/03 315/129 |
| 6,333,602 B1 | | 12/2001 | Kayser | |
| 6,407,417 B1 | | 6/2002 | Nagata et al. | |

(Continued)

*Primary Examiner* — John P Leubecker
*Assistant Examiner* — Pamela F Wu
(74) *Attorney, Agent, or Firm* — Whitmyer IP Group LLC (57) ABSTRACT

An intelligent endoscopic light source system for controlling the intensity of a light source, including a light source emitting light at a first intensity, an attenuator positioned to receive light from the light source at a first intensity and movable to pass light from the light source at a second intensity, a sensor mounted to the attenuator for measuring the first intensity, and a controller for receiving the intensity measurement from the sensor and moving the attenuator to pass light at a desired second intensity.

21 Claims, 5 Drawing Sheets

(56) References Cited

U.S. PATENT DOCUMENTS

| | | | |
|---|---|---|---|
| 6,419,941 B1 | 7/2002 | Farone et al. | |
| 6,464,633 B1 | 10/2002 | Hosoda et al. | |
| 6,514,807 B1 | 2/2003 | Yeh et al. | |
| 6,621,275 B2 | 9/2003 | Cotton et al. | |
| 6,800,946 B2 | 10/2004 | Chason et al. | |
| 6,817,977 B2* | 11/2004 | Ito | A61B 1/0669 362/574 |
| 6,847,170 B2 | 1/2005 | Kayser | |
| 7,063,467 B2 | 6/2006 | Nagasaka et al. | |
| 7,077,804 B2* | 7/2006 | Ota | A61B 1/0684 348/68 |
| 7,167,608 B2 | 1/2007 | Ogawa | |
| 7,266,262 B2 | 9/2007 | Ogawa | |
| 7,298,941 B2 | 11/2007 | Palen et al. | |
| 7,316,512 B2 | 1/2008 | Shih et al. | |
| 7,798,959 B2 | 9/2010 | Negishi | |
| 7,821,566 B2 | 10/2010 | Jung | |
| 7,828,726 B2 | 11/2010 | Negishi | |
| 7,842,990 B2 | 11/2010 | Kang | |
| 7,883,918 B2 | 2/2011 | Kang | |
| 7,928,001 B2 | 4/2011 | Kurita et al. | |
| 7,957,622 B2 | 6/2011 | Shimizu et al. | |
| 8,055,105 B2 | 11/2011 | Hodono | |
| 8,135,248 B2 | 3/2012 | Hodono | |
| 8,411,459 B2 | 4/2013 | Yu et al. | |
| 8,428,403 B2 | 4/2013 | Hodono | |
| 2002/0062061 A1* | 5/2002 | Kaneko | A61B 1/00009 600/118 |
| 2003/0069475 A1* | 4/2003 | Banik | A61B 1/00016 600/152 |
| 2005/0065400 A1* | 3/2005 | Banik | A61B 1/00059 600/109 |
| 2006/0293565 A1* | 12/2006 | Uchimura | A61B 1/00016 600/156 |
| 2007/0093690 A1* | 4/2007 | Hopkins | A61B 1/00059 600/180 |
| 2007/0177049 A1* | 8/2007 | Kreysar | G01J 1/04 348/368 |
| 2007/0225567 A1* | 9/2007 | Kobayashi | G02B 23/2461 600/178 |
| 2008/0058602 A1* | 3/2008 | Landry | A61B 1/00055 600/180 |
| 2008/0158548 A1* | 7/2008 | Chen | G01J 1/1626 356/73 |
| 2010/0060886 A1* | 3/2010 | Hwang | G01J 1/08 356/225 |
| 2012/0056091 A1* | 3/2012 | Mahowald | G01J 1/02 250/340 |
| 2013/0147777 A1* | 6/2013 | Lau | G02B 26/00 345/207 |

* cited by examiner

INTELLIGENT LIGHT SOURCE

FIELD OF THE INVENTION

The invention relates to an intelligent endoscopic light source, and more particularly, to an endoscopic light source that detects lamp intensity at startup and adjusts the level of attenuation necessary for a desired light output intensity.

BACKGROUND OF THE INVENTION

Conventional endoscopes are often supplied with illumination from an external light source. The light sources are generally coupled to the endoscope by means of a detachable waveguide or fiber optic light cable.

Such light sources generally include high intensity lamps, such as an incandescent or arc lamps. However, one issue with the use of such lamps is that their intensity cannot effectively be controlled by conventional means, such as reducing the power to the lamp through an electronic dimmer control. Instead, high intensity lamps are generally operated at full power and an alternate system is provided to reduce the intensity of the light transmitted to an endoscope for illuminating a site.

Another issue with high intensity lamps is that they produce a high amount of infrared energy, which if not properly reduced can cause damage. For example, light from a high intensity lamp can burn operating drapes, a patient's skin, or clothing.

Still further, as a high intensity lamp ages, the intensity of the lamp reduces and the color temperature drifts. For example, once a lamp has aged to the point where the output intensity is approximately 20-25% of a new lamp, the color temperature of the lamp output begins to drift. The color temperature drift can be so dramatic that an endoscopic camera system used with the light source may no longer correctly white balance the image. Thus, all images acquired by the camera will be off color, which can have tragic results if a surgeon using the light source makes an incorrect diagnosis based upon inaccurate tissue color and/or appearance.

Therefore, when using high intensity lamps in endoscopic light sources, it is desirable that both the intensity and infrared energy of the light transmitted to the endoscope is attenuated. It is also desirable that the color temperature of the lamp is monitored.

The reduction of the transmitted intensity of a lamp using a mechanical attenuator is effective for use with endoscopic light sources. Such systems are disclosed in U.S. Pat. No. 5,006,965. However, this and other known devices do not effectively control the light output intensity as a lamp degrades or inform a user when a lamp needs to be replaced. Such devices also do not inform a user when the color temperature of the lamp drifts. Still further, such devices do not inform a user if the infrared energy emitted by the system is too high. Thus, with such devices disclosed in the prior art, it is difficult for a user to maintain a consistent light output intensity, for a user to know when the color temperature of the light source has drifted and for a user to determine if too much infrared energy is being output.

It is therefore desired to provide an improved endoscopic light source that automatically detects the intensity of a lamp and reduces the intensity to a predetermined level. It is further desired, that the system will inform a user when the lamp's intensity falls below a predetermined level, the color temperature is no longer acceptable and if the infrared energy is above a predetermined value.

SUMMARY OF THE INVENTION

Thus, it is an object of the invention to provide an endoscopic light source system having a light source emitting light at a first intensity, an attenuator positioned to receive light from the light source at the first intensity and movable to pass light from the light source at a second intensity, a sensor is mounted to the attenuator for measuring the first intensity, and a controller receives the first intensity measurement from the sensor and moves the attenuator into the proper position to pass light at a desired second intensity.

It is a further object of the invention to measure the first intensity each time the system is turned on and adjusting the attenuator to obtain a consistent second intensity as the first intensity varies with time.

It is still a further object of the invention to alert a user when the first intensity is below a predetermined value, informing the user that the light source needs to be replaced.

It is another object of the invention that the sensor measures the color temperature of the light source and the system alerts a user when the color temperature of the light source has drifted outside a predetermined range, informing the user the light source needs to be replaced.

It is still another object of the invention that the sensor measures the infrared energy of the light source and the system alerts a user when the infrared energy of the light source is above a predetermined value, informing the user to either troubleshoot the light source or the hot-mirrors may need adjusting or replacing.

It is another object of the invention that the sensor includes a wireless transceiver allowing the sensor to communicate with the controller wirelessly.

It is also an object of the invention that the sensor includes a photovoltaic cell that allowing the sensor to be powered by the light source.

It is still another object of the invention that the attenuator can be either a rotary attenuator or a linear attenuator.

These and other objects are achieved by providing an endoscopic light source system, including a light source emitting light at a first intensity and having a light output path, an attenuator having a control path for variably passing light from the light source at a second intensity and a sensor module having a light intensity sensor for measuring the first intensity. The control path and the sensor module are positionable in the light output path. A controller receives the first intensity measurement from the sensor module when the sensor module is in the light output path, and the controller positioning the attenuator to a location on the control path in the light output path in order to adjust the second intensity to a desired level.

The sensor module further including a color temperature sensor on the sensor module for measuring the color temperature of the light source and transmitting the measurement to the controller in order to alert a user when the color temperature of the light source is outside a predetermined range.

The sensor module can further include a photovoltaic cell to power the sensor module and a wireless a wireless transceiver for communicating with the controller.

The sensor module also including an infrared sensor for measuring the infrared energy of the light source and transmitting the measurement to the controller in order to alert a user when the infrared energy of the light source is above a predetermined value.

DETAILED DESCRIPTION OF THE INVENTION

Figure 1:
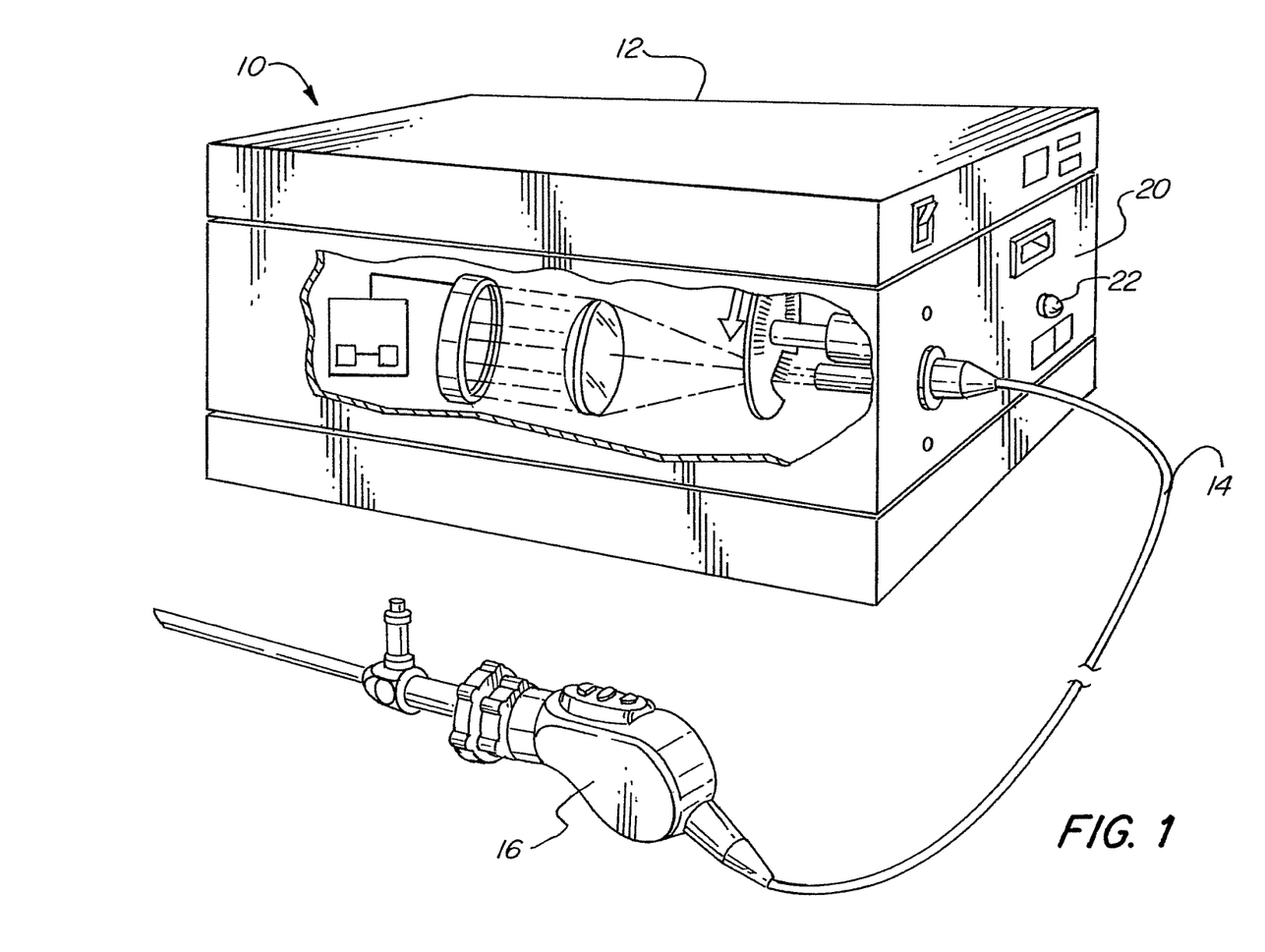
FIG. 1 is a perspective view of an endoscopic light system according to an embodiment of the present invention.

FIG. 1 shows a perspective view of an exemplary embodiment of an endoscopic light system 10 according to the invention. The system 10 includes an endoscopic light source 12 for providing visible light to a waveguide 14 that provides visible light to an endoscope 16. FIG. 1 includes a cutaway showing the internal components of the endoscopic light source 12 as shown in FIG. 2.

Figure 2:
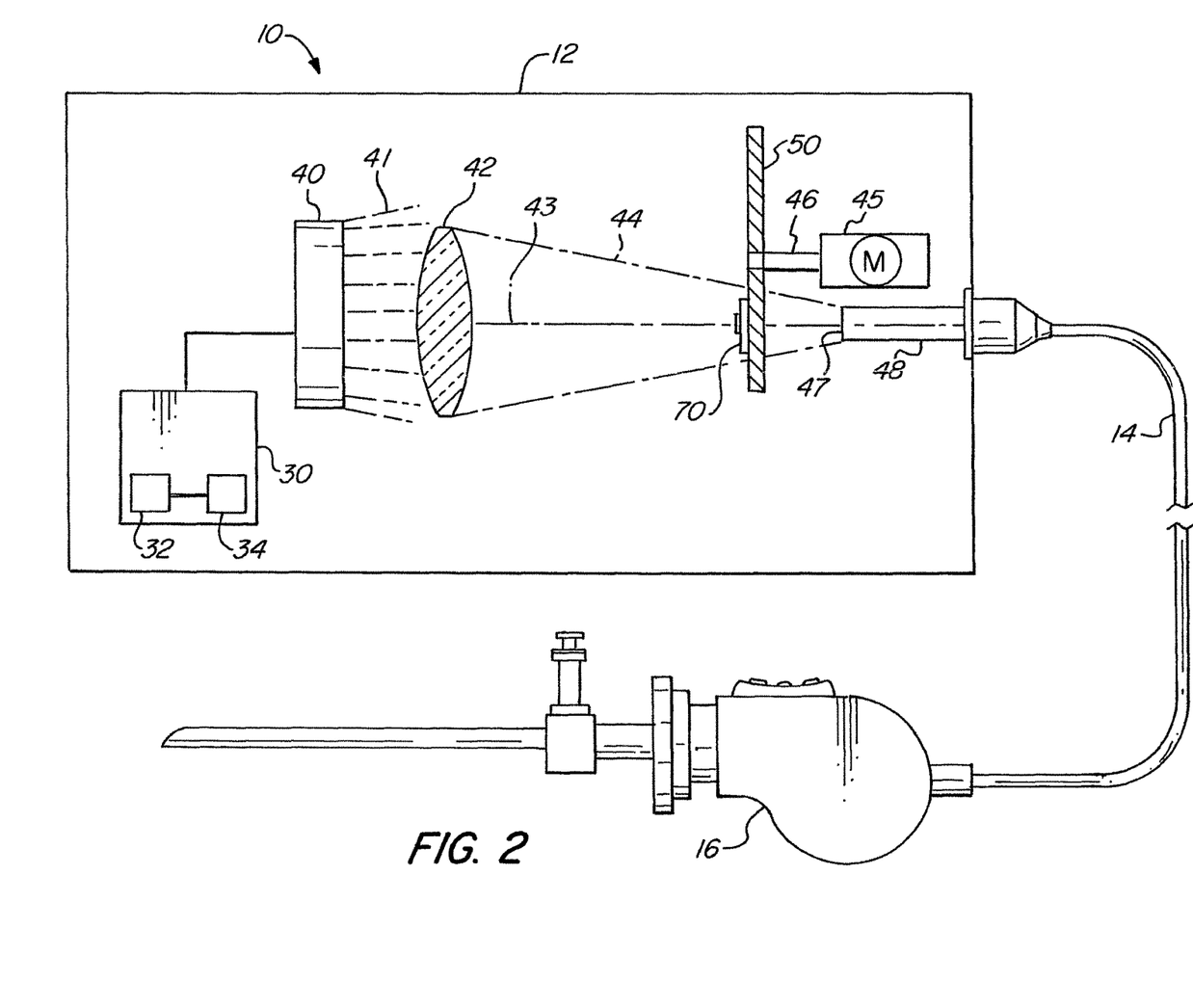
FIG. 2 is a schematic diagram of the endoscopic light system shown in FIG. 1

FIG. 2 is a schematic view of the endoscopic light system 10 of FIG. 1. FIG. 2 includes a lamp 40, which provides visible light 41 having an optical axis 43. The lamp 40 can be an incandescent lamp, arc lamp or any other suitable light source. A condenser lens 42 condenses the light beam 44 toward the input end 47 of a fiber optic bundle 48. An attenuator 50 is placed in the path of the light beam 44. The attenuator 50 is connected to the shaft 46 of a motor 45 for controlling the position of the attenuator 50. The rotational axis of the shaft 46 is offset and substantially parallel to the optical axis 43. The endoscopic light source 12 further includes a controller 30 connected to the lamp 40, motor 46, and front control panel 20. The front control panel 20 of the endoscopic light source 12, includes an on/off switch 18, indicator light 22 and other display and connection features for use by an operator.

The on/off switch 18 controls the power state of the endoscopic light source 12. The controller 30 controls the lamp 40 and motor 45 for actuating the attenuator 50. The controller 30 can communicate with the lamp 40 and motor 45 via either a direct connection or wirelessly. Thus, in certain embodiments the controller includes a processor 32 and a wireless transceiver 34. The wireless transceiver 34 can be any suitable technology for wireless communication, including for instance, infrared (IR), radio frequency (RF), Wifi and Bluetooth.

Figure 3A:
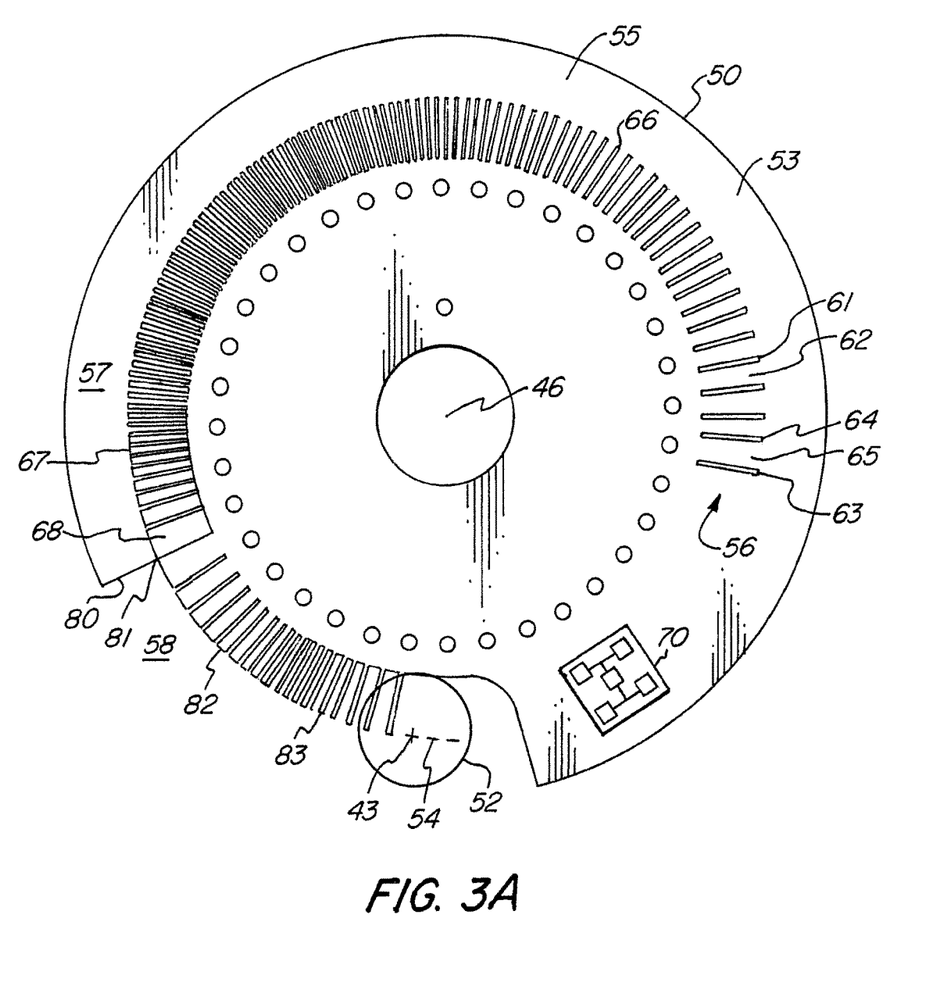
FIG. 3A is a front view one embodiment of the attenuator of FIGS. 1 and 2.

As shown in FIG. 3A, the attenuator 50 is preferably an opaque rotary vane attenuator for mechanically regulating, throttling, or controlling the intensity output 49 of the lamp 40. The light beam 44 forms a spot 52 on the outer portion of the attenuator 50. An arcuate control area 53 extends circumferentially around the attenuator 50. The control area 53 has a movement axis 54 that coincides with the optical axis 43 of the light beam 44. In this embodiment, the movement axis 54 divides the control area into an outer band 55 lying on the outside of the movement axis 54 and an inner band 56 lying on the inside of the movement axis 54.

The outer band 55 has a substantial arcuate solid area 57 with the remainder of its active length an open area 58. Thus, when the solid area 57 is in the path of the light beam 44, approximately 50% of the light beam 44 is blocked by the attenuator 50. When the open area 58 is in the path of the light beam 44, then this 50% is restored to the transmitted portion 49 of the light beam 44.

When the solid area 57 is in the path of the light beam 44 the outer band 55 reduces the amount of fine control required to be accomplished by the attenuator 50. Thus, the inner band 56 must attenuate only half of the light. Above the 50% attenuation level, open area 58 is used and the light transmitted by the outer band 55 is added to the light transmitted by the inner band 56.

The inner band 56 includes a progression of slots 61 combined with opaque bars 62. The width of the slots and bars are selected to produce a desired light intensity transmission. FIG. 3A is only an example of one suitable arrangement to provide a smooth variation of transmitted light intensity. The gradual changes allows for fine control of the transmitted light intensity.

For instance, slots 63 and 64 are relatively far apart, spaced by a wide bar 65. The bars between the slots narrow as they approach slot 66, but the slots remain about the same width. After this region, the bars remain about constant, but slots such as slot 67 become wider. Finally, slot 68 is very wide, and abuts the edge 80 of the outer band 55, creating a cross-over point 81 where light becomes controlled along with light passed by the outer band 55. Then bars 82 start to decrease while the slots are constant, followed by a region near slot 83 where the slots again increase in width.

In use, as the attenuator 50 turns away from slots 63 and 64 the light transmitted by the inner band 56 increases while the outer band 55 blocks transmission. Then at the cross-over point 81, the inner band 56 again has reduced throughput, which gradually increases that is now in addition to the light transmitted by the outer band 55.

Figure 4:
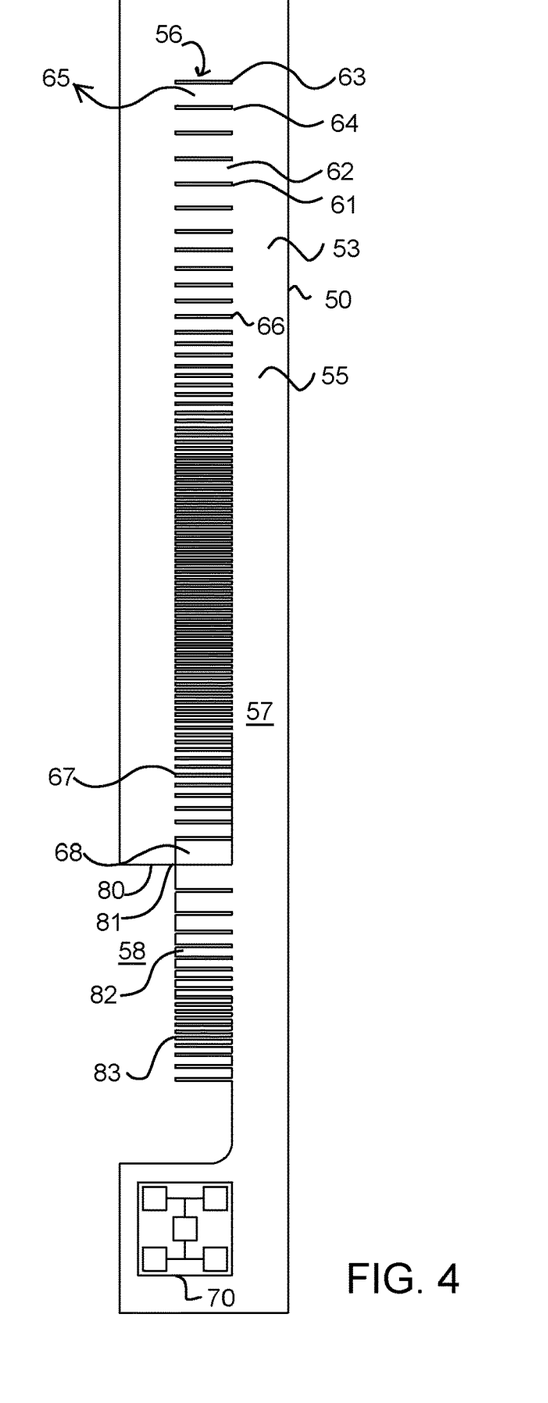
FIG. 4 is a front view of one embodiment of the attenuator of FIGS. 1 and 2.

The illustrated arrangement and sizes of the slots and bars are for purposes of providing an example. Many other patterns, slots, bars and portions of the outer band can be provided, which will produce a desired, but different dimming pattern. Furthermore, it should be understood that the attenuator may be linear, as shown in FIG. 4, instead of rotational. In such event, the control area is linear and moved back and forth across the optical axis.

Figure 3B:
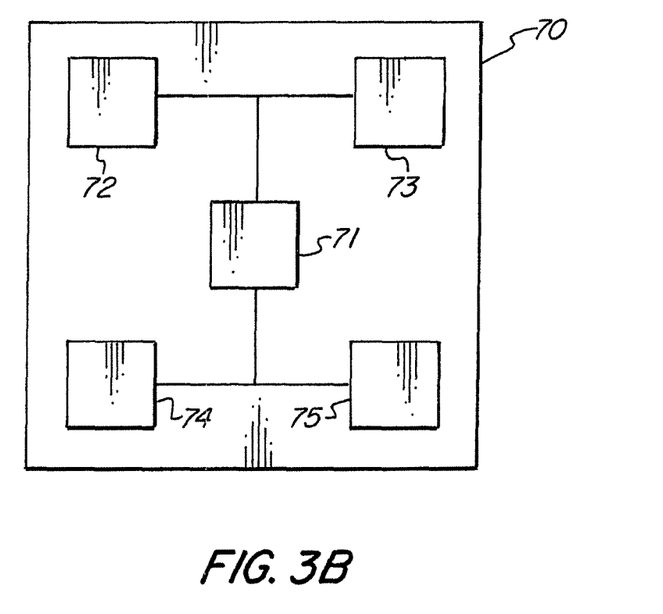
FIG. 3B is a schematic diagram of an embodiment of the sensor module affixed to the attenuator as shown in FIGS. 2 and 3A.

The attenuator 50 also includes a sensor module 70 affixed to a solid portion of the attenuator 50 in the movement axis 54 of the light beam 44. As shown in FIG. 3B, the sensor module 70 includes a processor 71 and a visible light sensor 72 used to measure properties of the light beam 44, including luminance intensity and color temperature. In certain embodiments the sensor module 70 can also include a photovoltaic cell 73 to power the sensor module, an infrared ("IR") sensor 74 to measure the IR energy and a wireless transceiver 75 to communicate with the controller 30. The wireless transceiver 75 can be any suitable technology for wireless communication, including for instance, infrared (IR), radio frequency (RF), Wifi and Bluetooth. Alternatively, the sensor module 70 can be directly wired to the controller 30.

In use, the attenuator 50 is rotated such that the sensor module 70 is positioned within the light beam 44. If the sensor module 70 is equipped with a photovoltaic cell 73, the light beam 44 will power the sensor module 70. Once the sensor module 70 is energized, the processor 71 will detect the luminance intensity and color temperature using the visible light sensor 72 and communicate these values to the controller 30. This communication can be via the wireless transceivers 34, 75 of the controller 30 and sensor module 70.

Once the controller receives the luminance intensity and of the lamp 40, the controller 30 determines the percentage of attenuation required for the desired intensity output 49. The controller 30 then communicates with the motor 45 moving the attenuator 50 into the proper position to provide the desired amount of intensity. As the lamp 40 reaches the end of its useful life, less and less attenuation is required to achieve the desired output.

If the sensor module 70 is equipped with an IR sensor 74, the sensor module 70 will detect the IR energy in the light beam 44. By detecting the IR energy and communicating it to the controller 30, the controller 30 can determine whether the IR energy is being properly blocked or redirected by the hot-mirrors (not shown). If the IR energy value is above a predetermined set-point, indicating inadequate hot-mirror performance, the operator will be notified. For instance, controller 30 may turn on the indicator light 18 on the control panel 20 indicating that the lamp 40 requires troubleshooting and the hot-mirrors may require replacement.

Preferably, the endoscopic light source 12 will determine the output intensity of the lamp 40 each time the lamp 40 is turned on. Thus, the controller 30 can determine the intensity of the lamp 40 and properly adjust the attenuator 50 in order to maintain a consistent desired light source 12 intensity output.

Generally once the lamp 40 has aged and the output intensity is approximately 20-25% of a new lamp 40, the color temperature of the lamp output begins to drift. As previously described, the color temperature drift can be so dramatic that an endoscopic camera system used with the endoscopic light source 12 may no longer correctly white balance the image, causing all images acquired by the camera will be "off color". Thus, once the output intensity of the lamp 40 is below a certain level and/or the color temperature value is outside a certain range, a user will be notified that the lamp 40 requires replacement.

Since the controller 30 preferably checks the lamp 40 intensity and color temperature at each power-up, the controller 30 will detect when a new lamp 40 has been installed and automatically zero out the lamp 40 "hours on" counter displayed on the control panel 20. Moreover at initialization, if the controller 30 determines a "hot lamp" or incorrect lamp 40 is installed (e.g. a lamp over the maximum wattage rating for the system), the user will be notified.

Preferably the attenuator 50 is designed so at the normal intensity level of a new lamp 40, the attenuator 50 is positioned at approximately 20% attenuation (i.e. "light blockage") with the control panel 20 showing that the lamp 40 is at 100% intensity output. As the lamp 40 ages and its output intensity degrades, the controller 30 will introduce a correction/offset to the attenuator 50 position so that at the lamp's 40 maximum age (i.e. lowest acceptable intensity output) the attenuator 50 would be positioned completely out of the light output path (i.e. 0% attenuation).

While the invention has been specifically described in connection with certain specific embodiments thereof, it is to be understood that this is by way of illustration and not of limitation, and that various changes and modifications in form and details may be made thereto, and the scope of the appended claims should be construed as broadly as the prior art will permit.

The description of the invention is merely exemplary in nature, and, thus, variations that do not depart from the gist of the invention are intended to be within the scope of the invention. Such variations are not to be regarded as a departure from the spirit and scope of the invention.

What is claimed is:

1. An endoscopic light source system, comprising:
    a light source emitting light at a first intensity;
    an attenuator positioned to receive light from said light source at the first intensity and movable to pass light from said light source at a second intensity;
    a sensor mounted to said attenuator for measuring the first intensity; and
    a controller for receiving the intensity measurement from the sensor and moving said attenuator to pass light at the second intensity.

2. The endoscopic light source system of claim 1, wherein the first intensity varies with time; and
    said controller alerting a user when the first intensity is below a predetermined value.

3. The endoscopic light source system of claim 2, wherein said light source emits light having a color temperature;
    said sensor measuring the color temperature of said light source and transmitting to said controller; and
    said controller alerting a user when the color temperature of said light source is outside a predetermined range.

4. The endoscopic light source system of claim 3, wherein said light source emits light having an infrared energy;
    said sensor measuring the infrared energy of said light source and transmitting it to said controller; and
    said controller alerting a user when the infrared energy of said light source is above a predetermined value.

5. The endoscopic light source system of claim 4, wherein said sensor communicates with said controller wirelessly.

6. The endoscopic light source system of claim 1, wherein said light source emits light having a color temperature;
    said sensor measuring the color temperature of said light source and transmitting to said controller; and
    said controller alerting a user when the color temperature of said light source is outside a predetermined range.

7. The endoscopic light source system of claim 1, wherein said light source emits light having an infrared energy;
    said sensor measuring the infrared energy of said light source and transmitting it to said controller; and
    said controller alerting a user when the infrared energy of said light source is above a predetermined value.

8. The endoscopic light source system of claim 1, wherein said sensor communicates with said controller wirelessly.

9. The endoscopic light source system of claim 1, wherein said sensor is powered by the light from said light source.

10. The endoscopic light source system of claim 1, wherein said attenuator is rotary.

11. The endoscopic light source system of claim 1, wherein said attenuator is linear.

12. The endoscopic light source system of claim 1, wherein the second intensity is less than the first intensity.

13. The endoscopic light source system of claim 1, further comprising:
    an on condition and an off condition;
    said controller measuring the first intensity when the system is changed from the off condition to the on condition; and
    said controller adjusting the second intensity to a predetermined value.

14. An endoscopic light source system, comprising:
    a light source emitting light at a first intensity and having a light output path;
    an attenuator having a control path for variably passing light from said light source at a second intensity and a sensor module mounted to said attenuator, the sensor module having a light intensity sensor for measuring the first intensity, the control path and the sensor module positionable in the light output path;

a controller for receiving the first intensity measurement from the sensor module when the sensor module is in the light output path;

said controller positioning said attenuator to a location on the control path in the light output path in order to adjust the second intensity based at least in part upon the first intensity of said light source.

15. The endoscopic light source system of claim 14, wherein the first intensity varies with time; and said controller alerting a user when the first intensity is below a predetermined value.

16. The endoscopic light source system of claim 15, wherein said sensor module further comprises:

a color temperature sensor;

said light source emits light having a color temperature;

said color temperature sensor measuring the color temperature of said light source and transmitting to said controller; and said controller alerting a user when the color temperature of said light source is outside a predetermined range.

17. The endoscopic light source system of claim 15, wherein said sensor module further comprises:

a photovoltaic cell to power said sensor module; and a wireless transmitter for communicating with said controller.

18. The endoscopic light source system of claim 15, wherein said sensor module further comprises:

an infrared sensor;

said light source emits light having an infrared energy;

said infrared sensor measuring the infrared energy of said light source and transmitting to said controller; and said controller alerting a user when the infrared energy of said light source is above a predetermined value.

19. The endoscopic light source system of claim 14, further comprising:

an on condition and an off condition;

said controller measuring the first intensity with the sensor module positioned in the light output path when the system is changed from the off condition to the on condition; and said controller adjusting the second intensity to a predetermined value.

20. The endoscopic light source system of claim 14, wherein said attenuator is rotary.

21. The endoscopic light source system of claim 14, wherein said attenuator is linear.

* * * * *